(12) United States Patent
Case et al.

(10) Patent No.: US 10,130,747 B2
(45) Date of Patent: *Nov. 20, 2018

(54) PERFORMING AN APHERESIS PROCEDURE ON A HUMAN SUBJECT WITH IDENTITY INPUT DATA

(71) Applicant: Fenwal, Inc., Lake Zurich, IL (US)

(72) Inventors: Brian C. Case, Lake Villa, IL (US); Lan T. Nguyen, Vernon Hills, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,227

(22) Filed: Dec. 8, 2017

(65) Prior Publication Data

US 2018/0099080 A1   Apr. 12, 2018

Related U.S. Application Data

(63) Continuation of application No. 14/455,413, filed on Aug. 8, 2014, now Pat. No. 9,867,922, which is a continuation of application No. 13/110,520, filed on May 18, 2011, now abandoned.

(51) Int. Cl.

| | |
|---|---|
| *G06F 7/04* | (2006.01) |
| *A61M 1/34* | (2006.01) |
| *G16H 10/60* | (2018.01) |
| *A61B 34/10* | (2016.01) |
| *G06F 19/00* | (2018.01) |

(52) U.S. Cl.
CPC .......... *A61M 1/3403* (2014.02); *A61B 34/10* (2016.02); *G06F 19/00* (2013.01); *G16H 10/60* (2018.01); *H05K 999/99* (2013.01); *A61M 2205/33* (2013.01); *A61M 2205/3334* (2013.01)

(58) Field of Classification Search
CPC combination set(s) only.
See application file for complete search history.

(56) References Cited

U.S. PATENT DOCUMENTS

| | | |
|---|---|---|
| 5,686,696 A | 11/1997 | Baker, Jr. et al. |
| 6,325,775 B1 | 12/2001 | Thom et al. |
| 6,471,855 B1 | 10/2002 | Odak |
| 6,695,806 B2 | 2/2004 | Gelfand et al. |
| 6,983,884 B2 | 1/2006 | Auchlinleck |

(Continued)

*Primary Examiner* — Wayne Young
*Assistant Examiner* — Cal Eustaquio
(74) *Attorney, Agent, or Firm* — Becker Patent Law, LLC

(57) ABSTRACT

A system for performing an apheresis procedure on a human subject includes an apheresis device having a communication channel in communication with a data storage device remote from the apheresis treatment device, an input device configured to receive an identity input data, wherein the identity input data comprises a combination of data, and a processing circuit. The processing circuit is configured to compare the identity input data to an identity of a human subject downloaded from the data storage device and, if the combination of data is consistent with two or more subject-specific information for a subject data entry, to provide access to an apheresis procedure operated according to the pre-programmed parameters on the apheresis device. The processing circuit is configured to derive an operating parameter for the apheresis procedure based on at least one of the subject-specific information of the human subject and to operate the apheresis procedure using the derived operating parameter.

18 Claims, 2 Drawing Sheets

(56) References Cited

U.S. PATENT DOCUMENTS

| | | |
|---|---|---|
| 7,050,611 B2 | 5/2006 | Bodicker et al. |
| 8,204,694 B2 | 6/2012 | Hauck et al. |
| 8,287,818 B2 | 10/2012 | Kantrowitz et al. |
| 8,405,508 B2 | 3/2013 | Burke |
| 8,746,547 B2 | 6/2014 | Mollstam et al. |
| 2002/0151804 A1 | 10/2002 | O'Mahony |
| 2003/0125017 A1 | 7/2003 | Greene |
| 2004/0183683 A1 | 9/2004 | Funahashi |
| 2005/0228238 A1 | 10/2005 | Monitzer |
| 2006/0093190 A1 | 5/2006 | Cheng et al. |
| 2007/0018832 A1 | 1/2007 | Beigel |
| 2007/0067452 A1 | 3/2007 | Fung |
| 2007/0138069 A1 | 6/2007 | Roncadi |
| 2007/0258626 A1 | 11/2007 | Reiner |
| 2007/0268130 A1 | 11/2007 | Yee |
| 2009/0275808 A1 | 11/2009 | DiMaio |

PERFORMING AN APHERESIS PROCEDURE ON A HUMAN SUBJECT WITH IDENTITY INPUT DATA

CROSS-REFERENCE TO RELATED APPLICATIONS

The present application is a continuation of application Ser. No. 14/455,413 filed Aug. 8, 2014, which is continuation of application Ser. No. 13/110,520 filed May 18, 2011, both of which are incorporated by reference herein in their entireties.

BACKGROUND

Field of the Disclosure

The present subject matter relates to systems and methods for controlling the performance of a medical procedure on a subject.

Description of Related Art

It is axiomatic that the parameters under which an at least partially automated medical procedure is performed, including without limitation blood donations and apheresis, should correspond or be appropriate to the characteristics of the donor or patient upon which the procedure is being performed. For example, when performing a blood donation procedure, it may be advantageous for a number of parameters, such as the sex and weight of the donor or patient, to be taken into consideration. If the incorrect operational parameters are used, the procedure may be less efficient than it would otherwise be and/or in certain circumstances could possibly be harmful to the donor or patient. Accordingly, care should be taken that the operational parameters correspond to the unique characteristics of the donor or patient.

Typically, information regarding the donor or patient is present in a datasheet or written prescription and entered into the automated device or system via a user interface by the operator of the system (e.g., a nurse, doctor, or technician) at the beginning of the procedure. The operator confirms the settings of the system and the identity of the subject and then instructs the system to initiate the medical procedure. By relying on manual data entry, there is of course a risk of operator error, resulting in operational parameters which do not correspond to the unique characteristics of the donor or patient. Thus, systems and methods which reduce the risk of data entry errors would be advantageous.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a system is provided for performing a medical procedure with respect to a subject. The system includes a database, a user interface, a treatment device, and a controller. The database is pre-programmed with one or more subject data entries, each subject data entry having subject-specific information associated with it. The user interface is adapted to receive an identity input from a subject. The controller is associated or in communication with the database, the user interface, and the treatment device, and is configured to compare the identity input to the subject-specific information of the subject data entries. If the identity input corresponds to the subject-specific information of a subject data entry, the controller commands the treatment device to perform a medical procedure with respect to the subject. If the identity input does not correspond to the subject-specific information of any of the subject data entries, the controller generates an error signal that prevents the performance of the medical procedure with respect to the subject.

In another aspect, a method is provided for performing a medical procedure with respect to a subject. One or more subject data entries are stored, with each having subject-specific information associated with it. An identity input is received from the subject. The identity input is compared to the subject-specific information of the subject data entries. If the identity input corresponds to the subject-specific information of a subject data entry, a medical procedure is performed with respect to the subject. If the identity input does not correspond to the subject-specific information of any of the subject data entries, an error signal is generated to prevent the performance of the medical procedure with respect to the subject.

DESCRIPTION OF THE ILLUSTRATED EMBODIMENTS

The embodiments disclosed herein are exemplary only, and the subject matter described herein may be embodied in various forms. Therefore, specific details disclosed herein are not to be interpreted as limiting the subject matter as defined in the accompanying claims.

Figure 1:
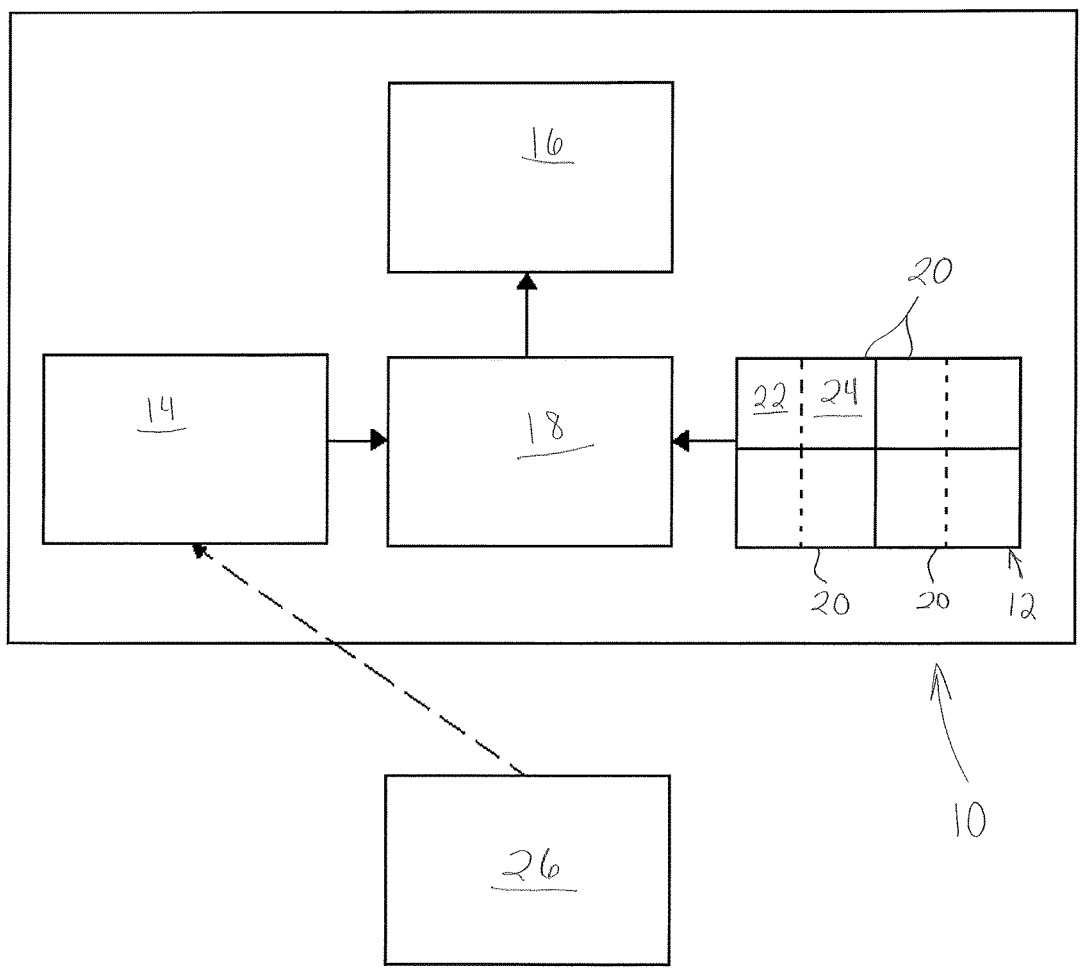
FIG. 1 is a schematic view of a medical device according to an aspect of the present disclosure.

FIG. 1 diagrammatically illustrates a system 10 for performing a medical procedure with respect to a subject. The system 10 of FIG. 1 includes a data storage location (such as a database 12), a user interface 14, a treatment device 16, and a controller 18. The system may be configured and used for carrying out any particular medical procedure. More particularly, the system may be configured for carrying out automated or semi-automated apheresis or blood collection procedures on a healthy donor or patient.

The data storage location may be variously configured and positioned without departing from the scope of the present disclosure. For example, the data storage location may be integrated into the system 10 and associated with the controller 18, as is the case with the database 12 of FIG. 1. In other embodiments, the data storage location may be remote from the system 10, for example, being located at or in a central server or storage facility of the owner of the system 10. If the data storage location is remotely located, it may communicate with the system 10 by any of a number of known or novel remote access means such as, but not limited to, wireless Internet access. In another embodiment, the data storage location is a removable storage device, such as an encoded identification card, which may be brought into association with the system 10 by a subject or operator. Other configurations of the data storage location may also be employed without departing from the scope of the present disclosure.

The data storage location may store a wide variety of data and information. In the embodiment of FIG. 1, the data storage location (in the form of a database 12) stores one or more subject data entries 20, with each subject data entry 20 corresponding to a subject (i.e., a donor or patient) upon which a medical procedure is to be performed using the system 10. The database 12 is pre-programmed with the subject data entry 20 for a particular subject at a time prior to the system 10 carrying out a medical procedure on that particular subject. Each subject data entry 20 includes subject-specific information 22, such as name, weight, sex, age, birth date, address, unique password, fingerprint, facial or retinal data, and/or answer(s) to security questions. The subject-specific information 22 corresponds to the identity of the subject and is compared to identity input 26 which is entered into the system by the subject, as will be described in greater detail below.

In addition to the subject-specific information 22, each subject data entry 20 may include one or more parameters 24 or such parameter(s) may be calculated or determined by the controller 18 based on the medical procedure and/or a combination of the procedure and subject-specific information 22. The nature of the parameter 24 may vary depending on the nature of the medical procedure to be performed. Also, the parameter 24 may relate to or be derived based on the sex of the subject, the weight of the subject, the acceptable rate at which fluid may be drawn from and/or returned to the subject (e.g., a citrate infusion rate), etc.

The user interface 14 includes a display for receiving commands and information from an operator or subject and displaying instructions for the operator or subject to perform. The display may be variously provided, such as in the form of a touch screen or, alternatively, a screen with an associated device which allows an operator or subject to interact with the user interface 14 (e.g., a keypad or keyboard). The user interface 14 also includes an input device for receiving an identity input 26 from the subject, which corresponds to the identity of the subject. As will be described in greater detail below, there are a variety of ways in which a subject may identify him- or herself, so the input device may be variously configured. In some embodiments, the display serves as an input device, while in other embodiments, the input device is separate from the display.

The principles of the present disclosure may be employed in a wide variety of devices and in a wide variety of procedures. Accordingly, the treatment device 16, which actually performs (at least part of) a medical procedure on the subject, may be variously configured. In one embodiment, the treatment device 16 may be an apheresis system, for example, a centrifuge system configured to draw blood from a subject, separate it into its constituents, and return at least one of the components to the subject. Exemplary centrifuge systems include those currently marketed as the ALYX® and AMICUS® systems by Fenwal, Inc. of Lake Zurich, Ill., as described in greater detail in U.S. Pat. No. 6,325,775 and U.S. Pat. No. 5,868,696, respectively, which are hereby incorporated herein by reference. Other treatment devices may also be employed without departing from the scope of the present disclosure, including (without limitation) dialysis systems, parenteral nutrition systems and others.

The controller 18 is associated with or in communication with the database 12, the user interface 14, and the treatment device 16. The controller 18 may be configured or programmed with a plurality of functions or procedures, and has various functions, including (but not limited to) receiving data from the various other components of the system 10, issuing commands to the various other components of the system 10, and monitoring the performance of the various other components of the system 10. In one embodiment, the controller 18 is configured to compare the identity input 26 which is provided by the subject to the subject data entries 20 stored in the database 12. If the identity input 26 corresponds to the subject-specific information 22 stored in one of the subject data entries 20 (i.e., if the system 10 "recognizes" the subject), the controller 18 will command the treatment device 16 to perform a medical procedure with respect to the subject. This may include determining or accessing the parameter(s) 24 associated with that particular subject data entry 20 (if provided) and sending the parameter(s) 24 to the treatment device 16 for use in performing the medical procedure.

If the identity input 26 does not correspond to the subject-specific information 22 stored in any of the subject data entries 20, the controller 18 may initiate any of a number of responses. In one embodiment, the controller 18 generates an error signal that prevents the performance of the medical procedure with respect to the subject. The error signal may trigger audible and/or visual alarms and alerts, including commanding the user interface 14 to show an error message (e.g. "Unable to confirm individual") on the display. In another embodiment, the controller 18 optionally commands the treatment device 16 to perform the procedure on the subject using default operational parameters instead of parameters uniquely suited to the subject.

Figure 2:
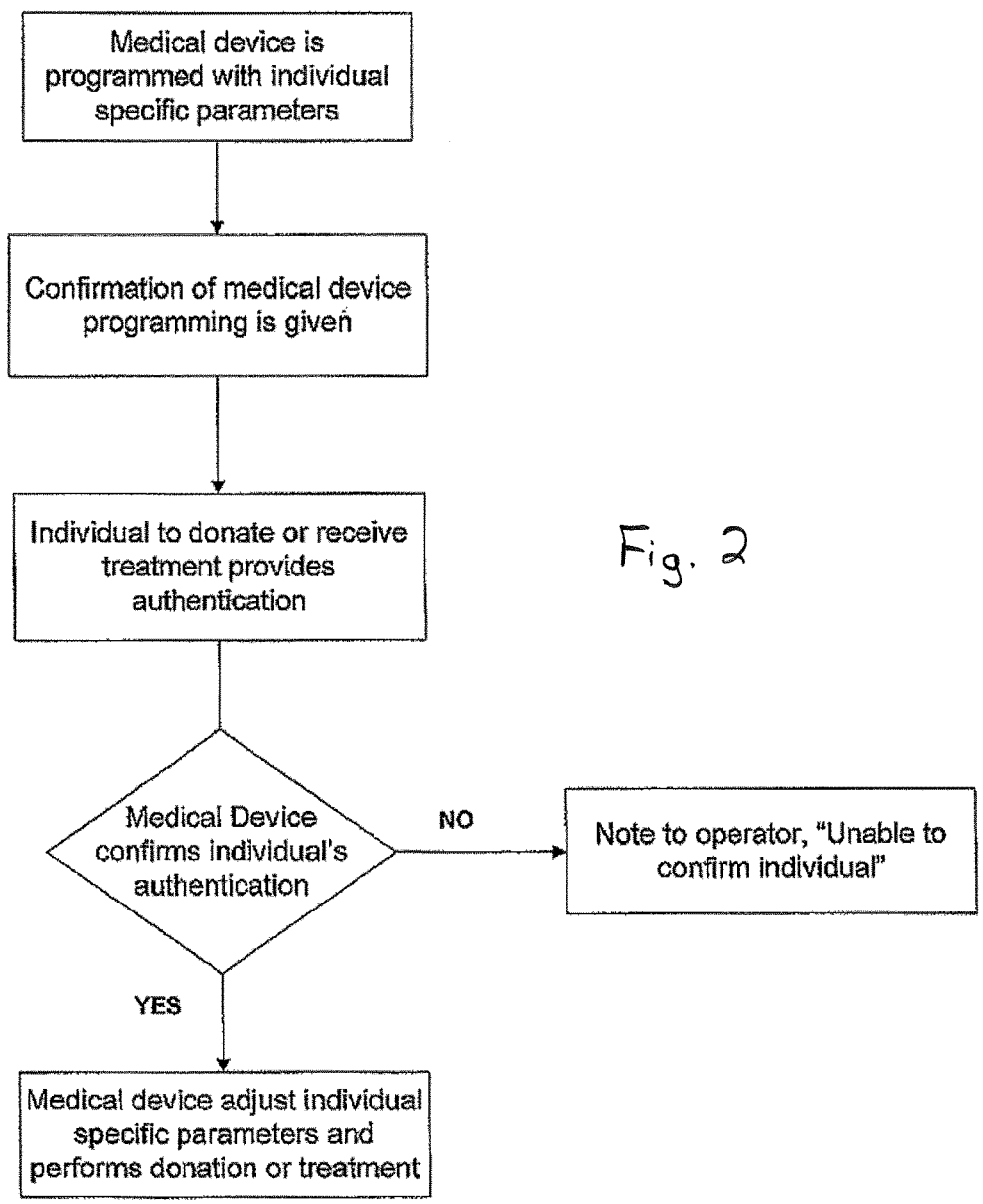
FIG. 2 is a flowchart which shows the process undertaken by the medical device of FIG. 1 when receiving identity information from a subject and then performing a medical procedure with respect to the subject.

FIG. 2 illustrates an exemplary manner of using a system 10 according to the present disclosure. Prior to a medical procedure being performed on the subject, a subject data entry 20 is pre-programmed into the database 12 for the subject. This may be done remotely or by using the user interface 14. A medical personnel is prompted to enter a variety of information, including at least the subject-specific information 22 which will be used to identify the subject. The medical personnel may also be prompted to enter one or more parameters 24 to be used when performing the medical procedure with respect to the subject. Depending on the nature of the identity input 26, the nature of the subject-specific information 22 and, hence, the manner and form in which it is entered into the database 12 may vary. For example, the information may be retrieved from another database, such as a central or remote database by direct interrogation and download, or in response to subject or medical personnel input. Further, the nature of the parameter(s) 24 may depend on the nature of the medical procedure to be performed with respect to the subject. When the subject-specific information 22 and optionally parameter(s) 24 (if provided) have been entered into the system 10, the medical personnel may confirm the data entered, thereby generating a subject data entry 20 which is stored in the database 12 and is unique to the subject.

At some later time, the subject is brought into the vicinity or proximity of the system 10 or an operable portion of the system 10. The subject may be connected to the treatment device 16 upon being brought into the vicinity of the system 10 or may be connected to the treatment device 16 at a later time (e.g., after the system 10 has confirmed the identity of the subject). While in the vicinity of the system 10, the subject attempts to identify him- or herself to the system 10 by providing an identity input 26 via the input device of the user interface 14. The identity of a subject may be expressed in any of a number of ways, so the system 10 may include one or more different input devices for receiving the identity input 26.

In one embodiment, the identity input 26 may take the form of biometric data, in which case the input device of the user interface 14 is provided as a biometric scanner or reader. For example, the input device may be provided as a fingerprint reader to receive and analyze the fingerprint of a subject. In another embodiment, the input device is provided as a retina scanner to view and analyze the retina of a subject. In yet another embodiment, the input device includes face recognition software to view and analyze the face of a subject. In another embodiment, the input device is provided as a heart rate monitor to consider the heart rhythm of a subject. In yet another embodiment, the input device includes a microphone or comparable audio device to receive and analyze the voice of a subject. In another embodiment, the input device is configured to receive a blood sample from a subject and analyze the DNA of the subject. Other biometric identifiers may also (or additionally) be provided by a subject to express his or her identity.

In another embodiment, the subject is provided with a unique subject identification card, badge, or removable storage device which is analyzed by the input device to attempt to identify the subject to the system 10. For example, the input device may comprise a bar code reader, with the subject being provided with a subject identification card having personal information encoded into a bar code which can be read by the input device. In another example, the subject may have a subject identification card encoded with personal information and having a built-in radio-frequency identification ("RFID") circuit. The input device comprises an RFID reader which is capable of reading the personal information on the card for subsequent analysis by the controller 18. The card may serve as a data storage location, as described above, being further encoded with one or more of the subject's unique operational parameters 24, rather than pre-programming the parameter(s) 24 into the database 12 or deriving/calculating them by the controller 18. In this case, the identity input 26 and the parameter(s) 24, if any, will be read by the input device and, if the identity input 26 corresponds to the subject-specific information 22 in one or more of the subject data entries 20, the controller 18 will send the parameter(s) 24 from the card to the treatment device 16. Furthermore, the card may be encoded with a multiple-treatment regimen, with the result of each treatment being tracked by the system 10 over time.

In one or more embodiments, the controller 18 may be programmed to require certain one or more of the subject-specific information 22 in the subject data entries 20 to correspond to the identity input 26. For example, the system 10 may require a combination of correct subject-specific information 22 before proceeding with the medical procedure. Specifically, the system 10 may require two or more subject-specific information 22 to be consistent with the identity input 26 and/or with each other. As non-limiting examples, the system 10 may require consistency among a name and sex; a name and password; a name and fingerprint and medical condition; a fingerprint and facial recognition; or such other combination as may be selected.

In yet another embodiment, the input device of the user interface 14 is programmed to recognize and read authentication software running on an electronic device, such as a mobile phone or laptop computer.

In another embodiment, the user interface 14 is programmed to receive a personal identification number, code, or password from the subject. If the display of the user interface 14 is a touch screen, the personal identification number may be directly entered using the display (thereby allowing the display to serve as the input device). Alternatively, an input device comprising a keypad or keyboard may be provided to allow the subject to enter the personal identification number.

When the subject has provided the identity input 26 to the system 10, the controller 18 compares the identity input 26 to the subject data entries 20 stored in the database 12. As described above, if the identity input 26 corresponds to the subject-specific information 22 stored in one or more of the subject data entries 20, as required by the system 10 (represented in FIG. 2 as a "YES" response to the "if-then" diamond containing the words "Medical Device confirms individual's authentication"), the system 10 has successfully identified the subject. The controller 18 will then command the treatment device 16 to perform a medical procedure with respect to the subject, which may include the controller 18 computing, retrieving, or accessing the parameter(s) 24 associated with that particular subject data entry 20 and sending it/them to the treatment device 16 for use in performing the medical procedure.

If the controller 18 is unable to match the identity input 26 to the subject-specific information 22 stored in any of the subject data entries 20 (represented in FIG. 2 as a "NO" response to the "if-then" diamond containing the words "Medical Device confirms individual's authentication"), the system 10 has failed to identify the subject. In the embodiment of FIG. 2, the controller 18 responds by disabling or declining to proceed with the medical procedure and may generate a signal that prevents the performance of the medical procedure with respect to the subject. The subject may then be given one or more additional opportunities to express his or her identity using the same or a different identity input 26. As described above, different responses to a failed identification may also be initiated without departing from the scope of the present disclosure.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A system for performing an apheresis procedure on a human subject, comprising:
    an apheresis treatment device configured to draw blood from a human subject, separate the blood by blood component, and return at least one of the components to the human subject; and
    a remote data storage device located remotely from the apheresis treatment device and configured to communicate with the apheresis treatment device over a network, the remote data storage device programmed with a plurality of subject data entries, each subject data entry associated with a human subject, each subject data entry comprising subject-specific information, the data storage device configured to download an identity of the human subject from the subject data entry and further configured to pre-program the apheresis treatment device with a plurality of parameters for the apheresis medical procedure, the parameters comprising at least one of a rate at which fluid may be drawn from the subject and a rate at which fluid may be returned to the subject;

the apheresis treatment device comprising:
an input device configured to receive an identity input data; and
a processing circuit configured to compare the identity input data to the downloaded identity of the human subject and, based at least in part on the result of the comparison, provide access to an apheresis procedure operated according to the pre-programmed parameters on the apheresis treatment device, wherein the processing circuit is configured to modify the subject data entry associated with the identity input data after the apheresis procedure is performed to record a result of the apheresis procedure.

2. The system of claim 1, wherein the processing circuit is configured based on the comparison to generate an error signal that prevents the performance of the apheresis procedure with respect to the human subject associated with the identity input data.

3. The system of claim 1, the input device comprising a card reader configured to read the identity input data from a card and further configured to read a multiple-treatment regimen encoded on the card, wherein the record comprises a result of each treatment in a multiple-treatment regimen over time.

4. The system of claim 1, wherein the subject-specific information comprises sex and weight of each human subject, wherein the apheresis treatment device is configured to operate the apheresis procedure based at least in part on a parameter derived from at least one of the sex and weight of the human subject upon which the apheresis procedure is performed.

5. The system of claim 1, wherein the input device comprises a touch screen configured to receive user input data from a user.

6. A system for performing an apheresis procedure on a human subject, comprising:
an apheresis treatment device configured to draw blood from a human subject, separate the blood by blood component, and return at least one of the components to the human subject; and
a remote data storage device located remotely from the apheresis treatment device and configured to communicate with the apheresis treatment device over a network, the remote data storage device programmed with a plurality of subject data entries, each subject data entry associated with a human subject, each subject data entry comprising subject-specific information, the data storage device configured to download an identity of the human subject from the subject data entry and further configured to pre-program the apheresis treatment device with a plurality of parameters for the apheresis medical procedure;

the apheresis treatment device comprising:
an input device configured to receive an identity input data, wherein the identity input data comprises a combination of data; and
a processing circuit, wherein the processing circuit is disposed within the apheresis treatment device, the processing circuit configured to compare the identity input data to the downloaded identity of the human subject and, if the combination of data is consistent with two or more subject-specific information for a subject data entry to provide access to an apheresis procedure operated according to the pre-programmed parameters on the apheresis treatment device.

7. The system of claim 6, wherein the processing circuit is configured to operate the apheresis procedure based on a default operational parameter instead of a parameter unique to the subject in the event the identity input data does not correspond to a subject data entry.

8. The system of claim 7, wherein the default operational parameter is indicative of at least one of a rate at which fluid may be drawn from the subject and a rate at which fluid may be returned to the subject.

9. The system of claim 6, wherein the input device comprises a wireless transceiver.

10. The system of claim 9, the input device comprising a card reader configured to read the identity input data from a card.

11. The system of claim 10, wherein the card reader comprises a radio frequency ID (RFID) card reader.

12. The system of claim 10, wherein the card reader is further configured to read a multiple-treatment regimen encoded on the card.

13. The system of claim 6, wherein the subject-specific information comprises sex and weight of each human subject, wherein the apheresis treatment device is configured to operate the apheresis procedure based at least in part on a parameter derived from at least one of the sex and weight of the human subject upon which the apheresis procedure is performed.

14. A system for performing an apheresis procedure on a human subject, comprising:
an apheresis device configured to draw blood from a human subject, separate the blood by blood component, and return at least one of the components to the human subject, the apheresis device further comprising:
a communication channel in communication with a data storage device remote from the apheresis treatment device,
an input device configured to receive an identity input data, wherein the identity input data comprises a combination of data; and
a processing circuit configured to compare the identity input data to an identity of a human subject downloaded from the data storage device and, if the combination of data is consistent with two or more subject-specific information for a subject data entry, to provide access to an apheresis procedure operated according to the pre-programmed parameters on the apheresis device, wherein the processing circuit is configured to derive an operating parameter for the apheresis procedure based on at least one of the subject-specific information of the human subject and to operate the apheresis procedure using the derived operating parameter.

15. The system of claim 14, wherein the processing circuit is configured to derive the operating parameter based on at least one of the sex and weight of the human subject.

16. The system of claim 14, wherein the processing circuit is configured to operate the apheresis procedure based on a default operational parameter instead of a parameter unique to the subject in the event the identity input data does not correspond to a subject data entry.

17. The system of claim 16, wherein the default operational parameter is indicative of at least one of a rate at which fluid may be drawn from the subject and a rate at which fluid may be returned to the subject.

18. The system of claim 14, wherein the combination of identity data comprises a name and a password, a name and a sex, or a name and a medical condition.

\* \* \* \* \*